United States Patent
Liu

(10) Patent No.: US 9,738,865 B2
(45) Date of Patent: Aug. 22, 2017

(54) FERMENTATION APPARATUS

(71) Applicant: Advanced Green Biotechnology Inc., Changzhi Township, Pingtung County (TW)

(72) Inventor: Chien-Yi Liu, Changzhi Township, Pingtung County (TW)

(73) Assignee: ADVANCED GREEN BIOTECHNOLOGY INC., Changzhi Township, Pingtung County (TW)

(*) Notice: Subject to any disclaimer, the term of this patent is extended or adjusted under 35 U.S.C. 154(b) by 89 days.

(21) Appl. No.: 14/857,812

(22) Filed: Sep. 17, 2015

(65) Prior Publication Data

US 2016/0186121 A1    Jun. 30, 2016

(30) Foreign Application Priority Data

Sep. 17, 2014   (TW) .............................. 103216494 U

(51) Int. Cl.
*C12M 1/36* (2006.01)
*C12M 1/00* (2006.01)
*C12M 1/12* (2006.01)

(52) U.S. Cl.
CPC ............ *C12M 41/48* (2013.01); *C12M 29/00* (2013.01); *C12M 29/04* (2013.01); *C12M 29/26* (2013.01)

(58) Field of Classification Search
CPC ...... C12M 41/14; C12M 37/02; C12M 29/04; C12M 29/00; C12M 41/48
See application file for complete search history.

(56) References Cited

U.S. PATENT DOCUMENTS

| | | | | |
|---|---|---|---|---|
| 5,571,703 | A * | 11/1996 | Chieffalo et al. ......... | B09B 3/00 426/11 |
| 2007/0227971 | A1* | 10/2007 | Denney ................. | C02F 1/5236 210/606 |
| 2009/0032464 | A1* | 2/2009 | Noguchi et al. ....... | B01D 65/08 210/637 |
| 2009/0286295 | A1* | 11/2009 | Medoff et al. ........... | C07H 3/02 435/162 |
| 2010/0261243 | A1* | 10/2010 | Kloos ....................... | C12P 7/06 435/161 |
| 2012/0267307 | A1* | 10/2012 | McGinnis ............ | B01D 61/002 210/638 |
| 2013/0115588 | A1* | 5/2013 | Davis et al. ........... | C12M 23/28 435/3 |
| 2013/0337552 | A1* | 12/2013 | Nishimura et al. ... | C13B 20/165 435/288.7 |
| 2014/0342444 | A1* | 11/2014 | Minamino et al. .... | B01D 61/58 435/294.1 |

* cited by examiner

*Primary Examiner* — Gautam Prakash
(74) *Attorney, Agent, or Firm* — Cheng-Ju Chiang

(57) ABSTRACT

This invention provides a simple fermentation apparatus which is able to work in a standard pressure. Moreover, it can continuously produce liquid fermentation products automatically in a large amount without filtering. The fermentation apparatus is able to be configured in large farms. The use of it has become simple and convenient.

15 Claims, 5 Drawing Sheets

FERMENTATION APPARATUS

CROSS-REFERENCE TO RELATED APPLICATION AND CLAIM OF PRIORITY

This application claims the benefit of Taiwan Patent Application No. 103216494, filed on Sep. 17, 2014, in the Taiwan Intellectual Property Office, the disclosure of which is incorporated herein in its entirety by reference.

1. TECHNICAL FIELD

At least one embodiment of the present invention relates to fermentation apparatus. More particularly, the fermentation apparatus is able to be used in standard pressure, purifying the water and producing the liquid fermentation product automatically.

2. DESCRIPTION OF THE RELATED ART

The products of the fermentation have been seen and used widely in our lives. For instance, the fertilizer used in agriculture and the additives used in foods such as soy sauce, wine, vinegar or the fermented dairy drink thereof. In tradition, the producing method of the apparatus for these products is used in a high pressure and liquid state fermentation. Especially in the liquid state fermentation, it would be deal with different kinds of apparatuses. For example, after the mixing step in the shaking table bed, it would be transferred to the fermenter then proceeding fermentation. In this condition, the discontinuous steps would cause contaminations in vitro. Therefore, it perhaps influences the quality of the products, resulting that we have to filter it via filter apparatuses for concerning the quality of the products.

Regarding to fermentation, the quality of water plays an important role in it. The water quality for traditional fermentation that is only required to achieve the drinking-water criteria. However, it is used to contain $Mg^{2+}$ or $Ca^{2+}$ ions and the other kinds of metal ions thereof. The mentioned ions disturb not only the fermentation efficiency but also the functional bacteria, causing the ion chelation between the products and the metal ions. Furthermore, the traditional fermentation apparatus are not connected with the water purification apparatus directly. Therefore, water which is used for fermentation is easily contaminated, before entering the fermentation apparatus. It would influence the quality of products.

SUMMARY

Regarding to description of the related art, the discontinuous operating way of the traditional fermentation apparatus causes several disadvantages such as being contaminated easily in vitro. Hence, after the fermentation is completed, it still has to be filtered by numerous apparatuses for ensuring the quality of product. Furthermore, it is also hard to maintain the quality of water in fermentation liquid. On the other hand, it perhaps causes the doubts of the qualities of fermentation products. With these reasons, the fermentation may be required to maintain its efficiency via a high pressure. Therefore this invention provides a fermentation apparatus, considering about the water quality and products of the liquid state fermentation which can be directly used without the other filtering processes. Moreover, this invention produces a huge amount of products automatically and continuously. Also, this invention is able to be configured in a large farm and be used simply.

The fermentation apparatus cited in this invention comprises a fermentation tank, a water filter, a water softener, a reverse osmosis apparatus, a heater and a centrifugal pump. The fermentation tank comprises a mixer and a ventilation pore, and wherein the water filter comprises water storage barrel. The water softener connects to the reverse osmosis apparatus, and the reverse osmosis apparatus is connected with the water storage barrel. The storage barrel connects to the fermentation tank via at least one pipe. Furthermore, the heater is connected with the water filter, and the centrifugal pump connects to the water filter and the fermentation tank with the at least one pipe.

The fermentation apparatus further comprises a control system, connecting to the fermentation tank, the heater, the centrifugal pump and the water filter electrically, and wherein the control system is able to produce the liquid state products continuously by automatic control.

The heater can be an electrothermal apparatus such as an electrothermal tube and it is able to heat the water storage barrel. In addition, a cooling apparatus is able to be connected with the water storage barrel via at least one pipe, and the cooling apparatus can be an ice water machine. The cooling apparatus is also connected with the control system electrically, cooling the temperature of the water storage barrel rapidly. Moreover, this invention further comprises an air filter. The mentioned air filter connects to the ventilation pore which is configured on the fermentation tank. Also, the air filter electrically connects to the control system. The air filter comprises a blower and an air filtering unit which is connected with the blower. The accuracy of the air filter for filtering out the bacteria which are larger than 1 µm, and the filtering target can be impurities, condensed water or lipids. The said air filter would avoid these materials to enter the fermentation process that may cause the interference of the quality of fermentation.

The fermentation tank is configured a material entrance, at least one liquid gate, a level gauge and a temperature detecting unit. The at least one pipe are set between the fermentation tank, the water filter and the centrifugal pump. Said at least one pipe is able to transfer the water which is inside the water storage barrel to the fermentation tank. On the other hand, regarding to the condition differences between water sources, the water filter is configured a sand filter and an active carbon filter. The sand filter is connected with the active carbon filter. Moreover, the active carbon filter is connected with the water softener. Moreover, for washing the water softener and recovering its ability, a salt barrel is connected with the water softener.

The water source for fermentation would be prepared by filtering, softening, reverse osmosis, and heating by the heater. Afterwards, the centrifugal pump would make a vacuum constriction force and transfer the water source to the fermentation tank via a connection between the material entrance and the at least one pipe, then the temperature detecting unit and the level gauge detect the temperature and the height of liquid level inside the fermentation tank respectively. Therefore, if the fermentation tank was overheated, the cooling apparatus would be able to decrease the temperature of it instantly. The materials and the functional bacteria of the fermentation are put into the fermentation tank through the material entrance, and the air which entered the fermentation tank is filtered. The filtering condition that is to filter out the impurities which are larger than 1 µm, such as the condensed water or lipids. Finally, the mixer is operated to mix for fermentation, and the liquid fermentation products would be released out of the fermentation tank via the at least one liquid gate.

The control system of this invention comprises a main circuit box and an operating circuit box which is connected with the main circuit box electrically. The said operating circuit box is a user interface machine, comprising a display unit and a control unit. The display unit connects to the display unit. The operating circuit box further comprises a communication unit and an RFID (radio-frequency identification) tag recognition unit. The communication unit is connected with the RFID tag recognition unit, and the communication unit is a subscriber identity module (SIM) card which is able to response the operating status to a manager who is absent. Therefore the manager can be far away from the fermentation apparatus but understand the operating status of it. The RFID tag recognition unit is an RFID tag reader which is to recognize the information contained in the RFID tag. The mentioned information comprises the type of the target product and the needs of materials, and the information would be transferred to the control unit. The display unit is a touch panel, setting the operating condition and showing the operating status. The said control unit is a multi-function chip or a programmable logic controller. It can control the main circuit box to complete several fermentation steps such as the height of the liquid, heating temperature, status of fermentation, mixing period, washing and the communication via SIM card automatically, reporting these operating information to the display unit. Therefore, this invention provides a simple, automatic and continuous manufacturing fermentation apparatus in a standard pressure. Moreover, though the manager is absent, the operating status of this invention can be remoted and watched. With this invention, the amount of the products would be fruitful without doing the other filtering steps. Thus it can be set in large farms and be used easily.

DESCRIPTION OF THE PREFERRED EMBODIMENTS

The examples depicted in the following section are provided for the purpose of detailed explanation of the features of preferred embodiments, in order to enable one having ordinary skill in the art to understand the preferred embodiments.

Figure 1:
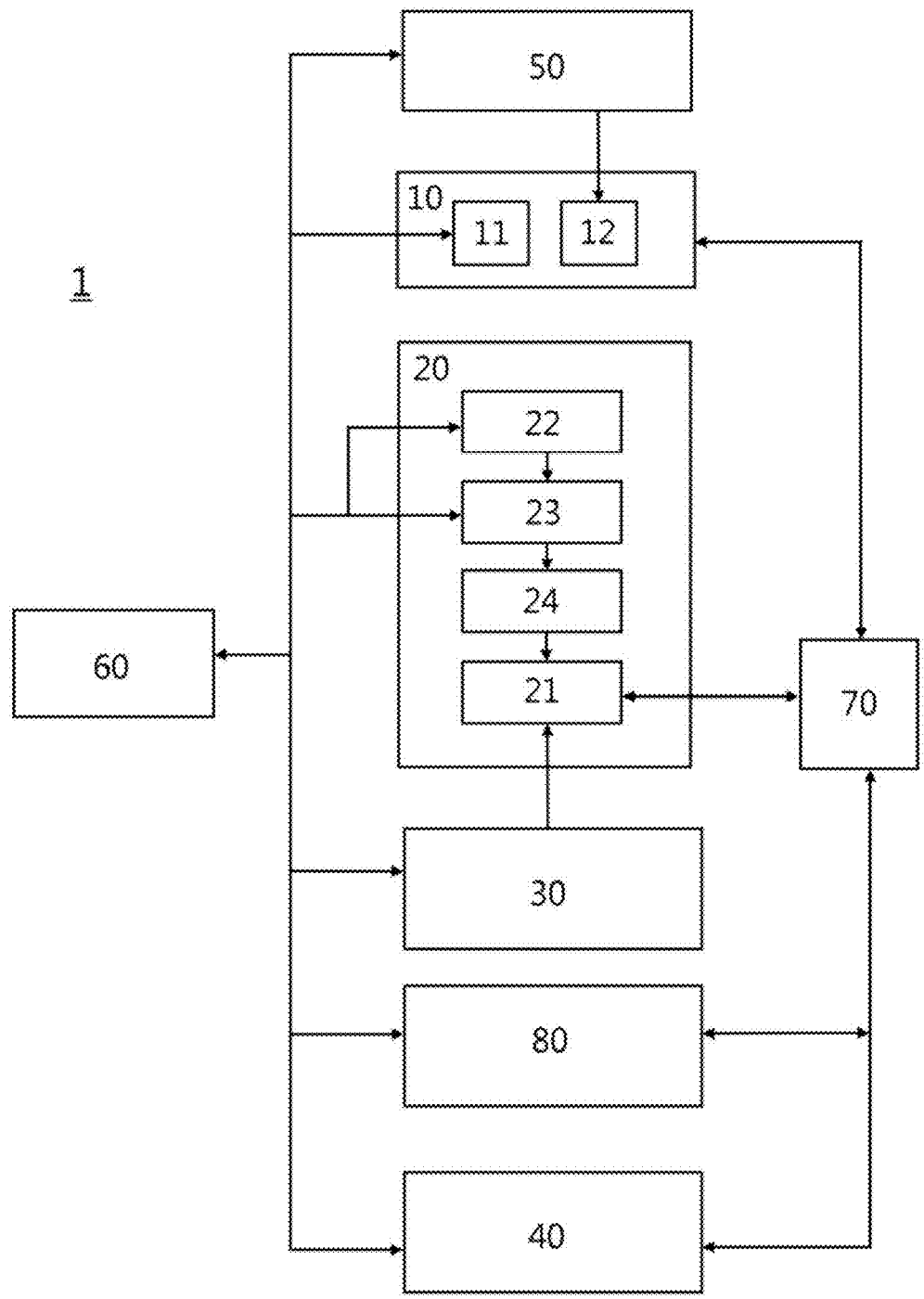
FIG. 1 is a diagram illustrating the structure of the fermentation apparatus.

FIG. 1 is a diagram illustrating the structure of the fermentation apparatus. This embodiment provides a fermentation apparatus 1, comprising a fermentation tank 10, a water filter 20, a heater 30, a centrifugal pump 40, an air filter 50 and a control system 60. The mentioned fermentation tank 10 comprises a mixer 11 and a ventilation pore 12. The water filter 20 contains a water storage barrel 21, an active carbon filter 22, a water softener 23 and a reverse osmosis apparatus 24. The function of the reverse osmosis apparatus 24 is similar to the active carbon filter 22. Therefore, the water filter 20 is able to be set without active carbon filter 22.

The heater 30 in this embodiment is connected with the water storage barrel 21 of the water filter 20. The water filter 20 connects to the fermentation tank 10 via at least one pipe 70, and the active carbon filter 22 of the water filter 20 connects to the water softener 23 which is connected with the reverse osmosis apparatus 24. The reverse osmosis apparatus 24 is connected with the water storage barrel 21 which is connected with the fermentation tank 10 via at least one pipe 70. The air filter 50 is connected with the ventilation pore 12 configured on the fermentation tank 10, and the centrifugal pump 40 connects to the water filter 20 and the fermentation tank 10 independently via the at least one pipe 70. The control system 60 is connected with fermentation tank 10, water filter 20, heater 30, centrifugal pump 40 and air filter 50 electrically.

This embodiment further comprises a cooling apparatus 80 which is an ice water machine. The cooling apparatus 80 is connected with the water storage barrel 21 via at least one pipe 70, and it is also electrically connected with the control system 60. When the temperature is over increased, the water stored in the water storage barrel 21 would be transferred to the cooling apparatus 80 then go back. With this mechanism, decreasing the temperature of the water storage barrel 21 rapidly.

Hence, this embodiment provides a fermentation apparatus which is simple and can be operated in the standard pressure. For producing the liquid fermentation products automatically in one machine.

Figure 2:
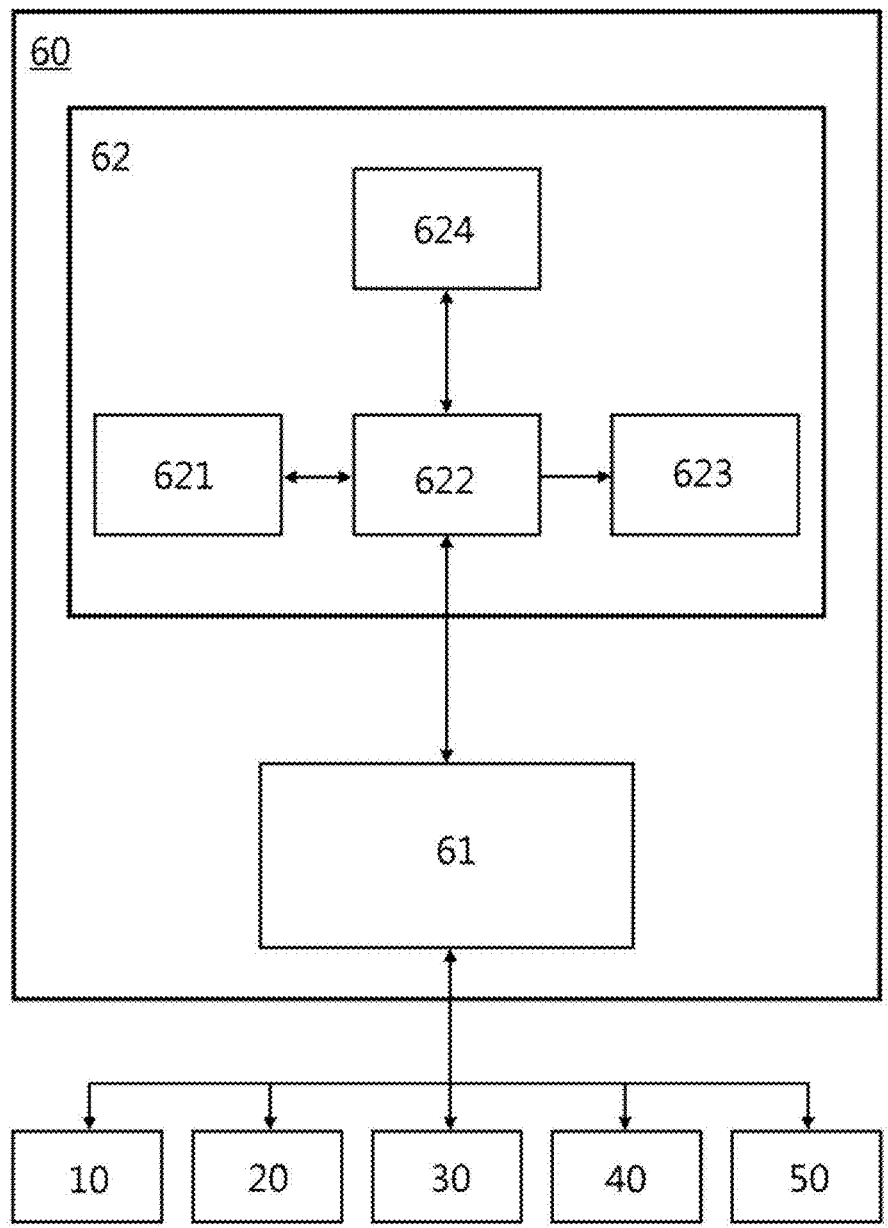
FIG. 2 is a diagram illustrating the structure of the control system.

Regarding to FIG. 2. It is a diagram illustrating the structure of the control system. FIG. 2 shows that the control system 60 of this embodiment comprises a main circuit box 61 and an operating circuit box 62. The main circuit box is connected with the operating circuit box electrically, and the main circuit box is also connected with the fermentation tank 10, water filter 20, heater 30, centrifugal pump 40 and the air filter 50 electrically. The mentioned operating circuit box comprises a display unit 621, a control unit 622, a communication unit 623 and an RFID tag recognition unit 624. The display unit 621, communication unit 623 and the RFID tag recognition unit 624 are connected with the control unit 622 independently. The display unit 621 is a touch panel which shows the operating status and operating conditions of this embodiment. The RFID recognition unit 624 is an RFID tag reader. The fermentation material packs are all with at least one RFID tag. Hence, the RFID recognition unit 624 can read the information which is inside the mentioned RFID tags, recognizing the fermentation type and the needs of the raw materials, and sending the information to the control unit 622. The control unit 622 is a multi-function chip or a programmable logic controller, and it is able to control the main circuit box 61 and setting the conditions of it for producing the fermentation products. The said conditions could be the height of liquid level, heating temperature, fermentation conditions, mixing period, washing processes and the communication of the SIM card. The mentioned information would be saved and sent back to the display unit for displaying. In this embodiment, the communication unit 623 is a SIM card, communicating with the other devices and the users are able to transfer the operating status to the manager when he or she is absent.

As the results, the control system 60 of this embodiment automatically controls the height of liquid level, heating temperature, fermentation process, mixing period and the communication of the SIM card. The fermentation apparatus 1 can produce the liquid fermentation products continuously. Furthermore, the fermentation apparatus 1 can also notice the manager when he or she is absent. The mentioned notice is about the operating status of the fermentation apparatus 1. If it was abnormal that the user can fix or retire it immediately.

Figure 3:
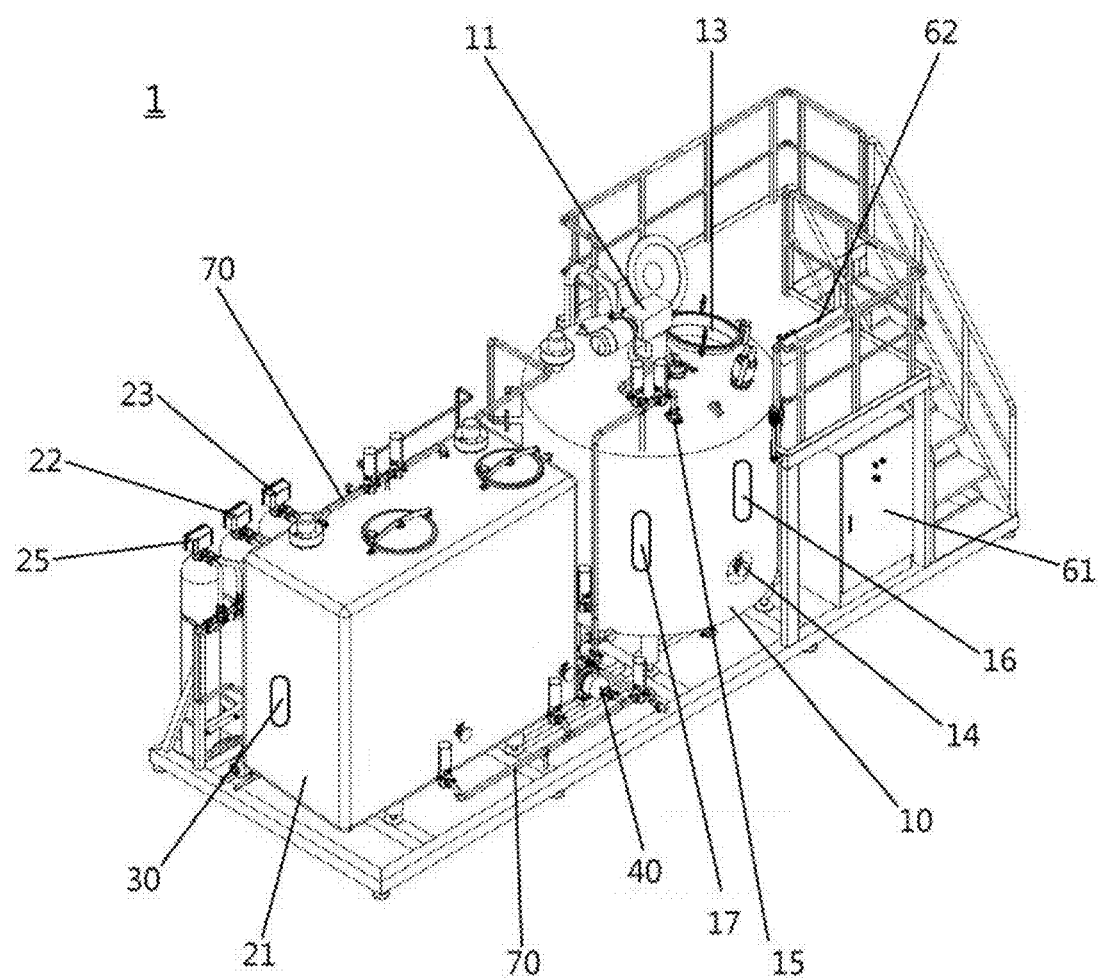
FIG. 3 is a diagram illustrating one side of the front view of the fermentation apparatus embodiment.
Figure 4:
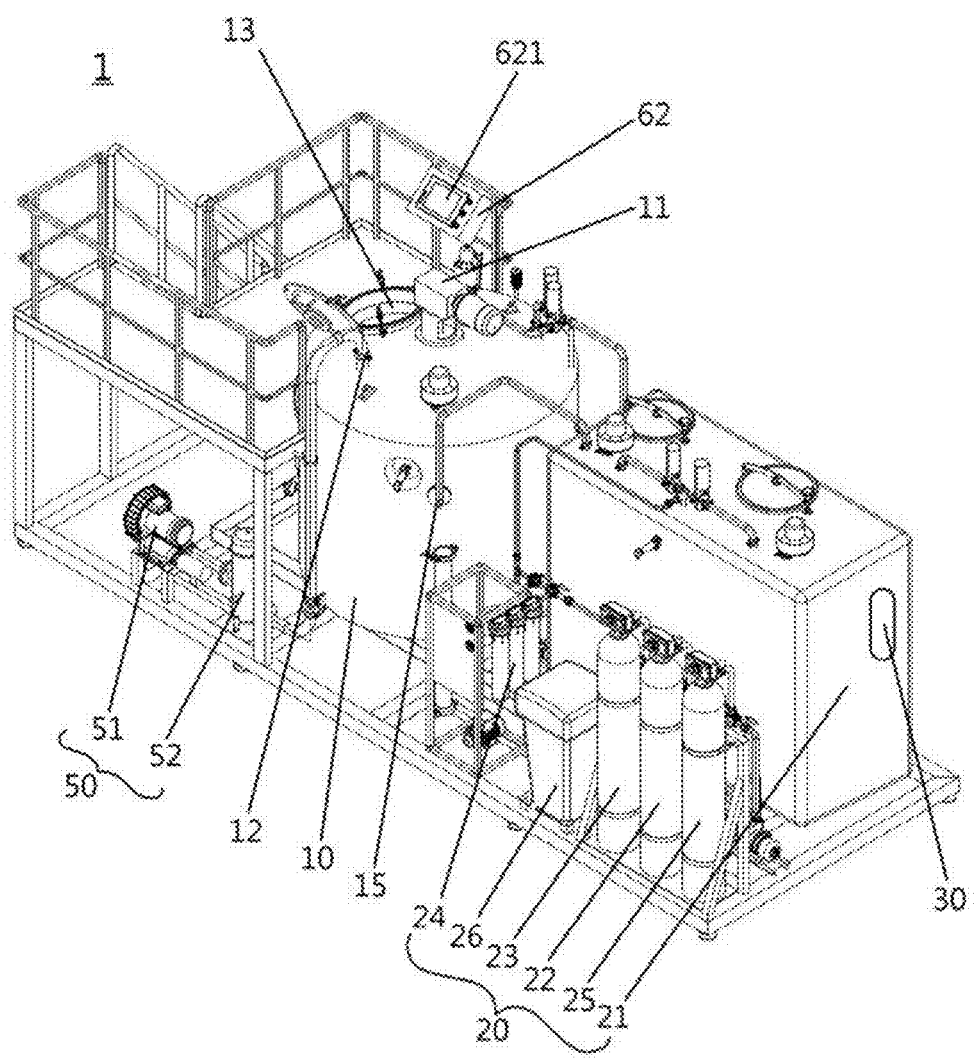
FIG. 4 is a diagram illustrating one side of the back view of the fermentation apparatus embodiment.

FIG. 3 is a diagram illustrating one side of the front view of the fermentation apparatus embodiment, and FIG. 4 is a diagram illustrating one side of the back view of the fermentation apparatus embodiment. With FIG. 3 and FIG. 4, the fermentation apparatus 1 comprises a hermetical three-layered stainless material made fermentation tank 10, a water filter 20, a heater 30, a centrifugal pump 40, an air filter 50 and at least one pipe 70. The mentioned water filter 20 is connected with the fermentation tank 10 via at least one pipe 70, and the heater 30 is connected with the water filter 20. The air filter 50 is connected with the fermentation tank 10 and the centrifugal pump 40 is connected to the water filter 20 and the fermentation tank 10 via the at least one pipe 70 independently.

A mixer 11, ventilation pore 12, material entrance 13, spout 14, at least one liquid gate 15, level gauge 16 and a temperature detecting unit 17 are configured on the fermentation tank 10. The water filter 20 comprises a hermetical double-layered stainless water storage barrel 21, active carbon filter 22, water softener 23, reverse osmosis apparatus 24, sand filter 25 and a salt barrel 26. The sand filter 25 connects to the active carbon filter 22, and the active carbon filter 22 is connected with the water softener 23. The mentioned water softener 23 is connected with the reverse osmosis apparatus 24 and the salt barrel 26 independently. The reverse osmosis apparatus 24 connects to the water storage barrel 21 which is connected with the fermentation tank 10 via at least one pipe 70. The centrifugal pump 40 connects to the water filter 20 and the fermentation tank via at least one pipe 70 independently. Wherein the said at least one pipe 70 comprises at least one valve and pipe fittings. Motorized ball valves are configured on the at least pipe 70 as the at least one valve in this embodiment, and the mentioned at least one valve is able to switch the water inside per se automatically. The air filter 50 comprises a cycle blower 51 and air filtering device 52. The blower 51 is connected with the air filtering device 52. The accuracy of the air filtering device 52 is larger than 1 μm, and the filtering target can be bacteria, impurities, particles, condensed water or lipids. To avoid the mentioned materials entering the fermentation process, interfering the quality of products.

The water source in this embodiment could be the river water, underground water, or the tap water. The sand filter 25 in the water filter 20 is able to filter organic or inorganic macro-particles contained in the mentioned water source. Afterwards, the active carbon filter 22 removes the dissolved organic materials or the impurities which are hard to be degraded via the absorption mechanism. The mentioned active carbon filter 22 is useful for removing the peculiar smell, gel, pigments, and heavy metal ions. Also, it is able to decrease the values of BOD and COD in the water and purify it. Furthermore, the water softener 23 removes the over contained minerals such as the calcium or the magnesium which may cause the hard water. Finally, the reverse osmosis apparatus 24 removes inorganic or organic micro-particles, nanoparticles, impurities, bacteria, minerals and the chemistry materials. After the mentioned water filtering processes, the water source which is used in fermentation is pure, containing a little amount of mineral ions. The salt barrel 26 is to wash the water softener 23. The softening ability of the water softener 23 is recovered by the salt washing process due to the salt barrel 26. The mentioned water filter 20 can be further configured other equipment regarding to the fermentation needs.

Therefore, after the water filtering, softening and reverse osmosis process. The water source is transferred and stored in the water storage barrel 21 via at least one pipe 70. The heater heats it to 40° C.~50° C., or over 60° C. for removing the unnecessary bacteria. When the essential temperature of the fermentation water is prepared, the centrifugal pump 40 transfers the fermentation water through the at least one pipe 70 to the liquid gate 15 which is configured on the fermentation tank 10 via vacuum constriction force, and the temperature detecting unit 17 and the level gauge 16 which are configured on the fermentation tank 10 would detect the temperature and the height of liquid level inside it respectively. Afterwards, put the raw materials and the functional bacteria which are able to live in high temperature into the fermentation tank 10 through the material entrance 13. The air is sent by the blower 51 and entering the fermentation tank 10 via the ventilation pore 12. In this step, the air would go through the air filter 52, filtering out the impurities, condensed water and lipids which are bigger than 1 μm. The mixer 11 proceeds to mix the raw materials and the functional bacteria for fermentation. After the fermentation has been completed, the liquid state fermentation product would be released from the spout 14. On the other hand, the level gauge 16 and the temperature detecting unit 17 are configured on the mentioned water storage barrel 21, for detecting the status of water source inside it respectively.

Moreover, a control system 60 is electrically connected with fermentation tank 10, water filter 20, heater 30, centrifugal pump 40 and the air filter 50 independently. The control system comprises a main circuit box 61 and an operating circuit box 62, and the main circuit box 61 is connected with the operating circuit box 62 electrically. The operating circuit box 62 is a user interface machine, comprising a display unit 621 and a control unit (not illustrated). The display unit 621 is connected with the control unit, and the display unit is a touch panel. The mentioned control unit is a multi-function chip or a programmable logic controller. Users can know the operating status and set the options from it. Therefore the control unit is able to control the main circuit box 61, executing the settings such as the liquid level, heat temperature, fermentation processes, mixing period, washing processes, and communication of the SIM card for producing the fermentation products. Also, the settings and operating status of the fermentation apparatus 1 would be replied to the display unit 621 and saved. On the other hand, damages of the apparatus are commonly happened because of the human washing. Therefore the control system 60 of this embodiment provides automatic washing processes. The washing water is able to be inserted in the fermentation tank 10 via the at least one pipe 70 which are connected between the water storage barrel 21 and the fermentation tank 10. It is able to conserve a lot of time and human resources, avoiding the damage of the apparatus.

Figure 5:
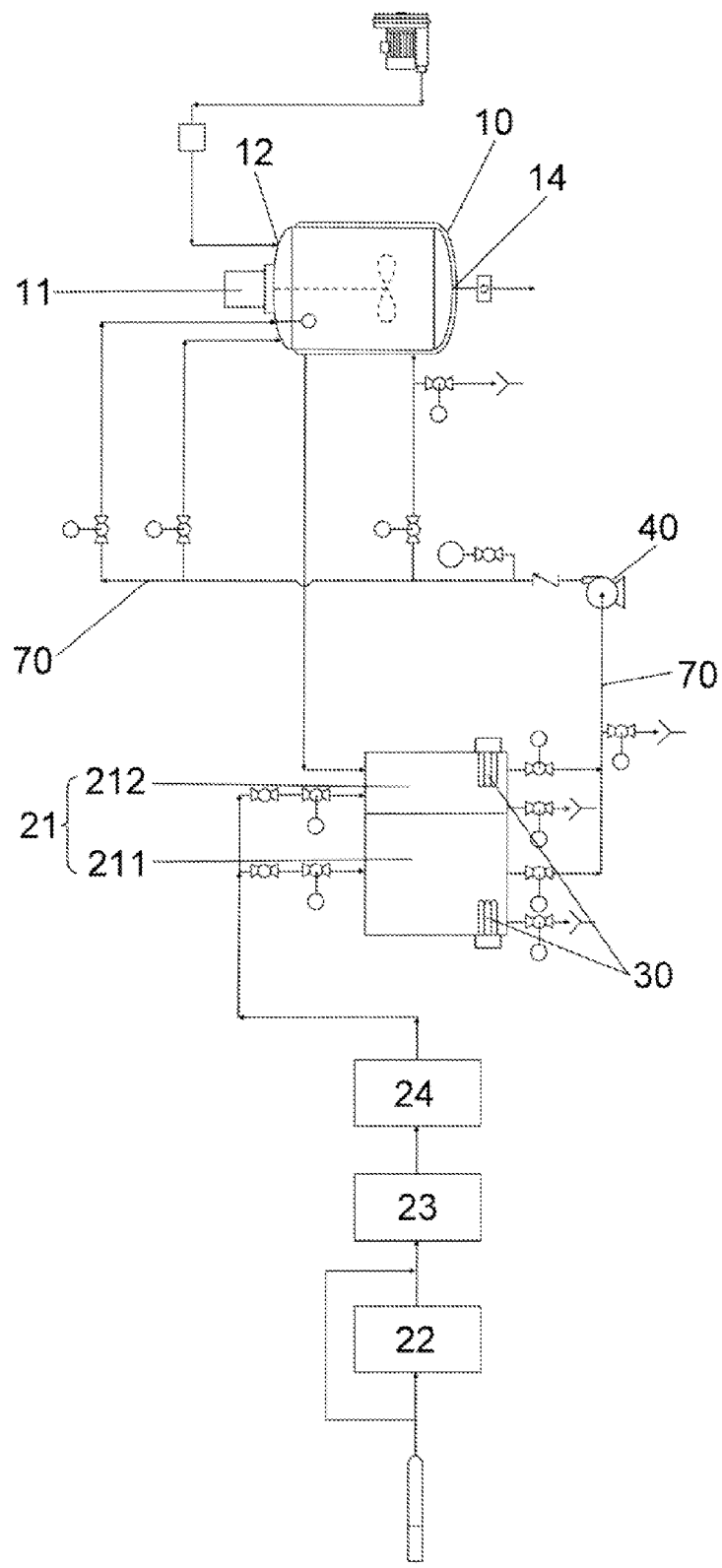
FIG. 5 is a diagram illustrating the other embodiment of the fermentation apparatus.

FIG. 5 is a diagram illustrating the other embodiment of the fermentation apparatus. In the embodiment of FIG. 5, the water source is filtered and softened by an active carbon filter 22, a water softener 23 and a reverse osmosis apparatus 24, and it would be stored in a water storage barrel 21 which is actually a 2000 liter square-shaped double tank in this embodiment. The mentioned water storage barrel 21 comprises a heater 30. In this embodiment, the mentioned water storage barrel 21 contains a 1500 liter reverse osmosis barrel 211 and a 500 liter recycle barrel 212. The mentioned 1500 liter reverse osmosis barrel 211 and a 500 liter recycle barrel 212 comprise an 8 kW and a 6 kW electrothermal apparatus respectively. The mentioned recycle barrel 212 is to heat the water, and the heated water would be transferred by the centrifugal pump 40. Afterwards, the heated water is inserted into the 2000 liter fermentation tank 10 via the connection of at least one pipe 70. Otherwise, if the required temperature of the fermentation tank 10 cannot be satisfied, the water which is inside the recycle barrel 212 would be heated until the required temperature, and the centrifugal pump 40 would transfer the heated water via pipes. In another situation, the at least one pipe 70 is able to transfer the water which is out of the required temperature in the fermentation tank 10 back to the recycle barrel 212. The centrifugal pump 40 is able to transfer the heated water into the fermentation tank 10 again. By the mentioned processes, it is able to put the raw materials of the fermentation such as bean flour, carbon source, nitrogen source, salt and the functional bacteria thereof into the fermentation tank 10. When the fermentation has stared, a mixer 11 would mix the mentioned raw materials and a cycle blower 51 which works in 2.2 kW×220V×60 Hz with the max blowing rate 3.2 $m^3$/min would send air into the fermentation tank 10 through the ventilation pore 12 by passing an air filter 52. The mentioned air filter 52 is able to filter out impurities, condensed water or lipids which are larger than 1 μm. The products of fermentation are able to be released from the spout 14. Otherwise, the mentioned reverse osmosis apparatus 24 can filter the water independently. Therefore the water filter 20 could be configured without the active carbon filter 22.

Hence, this embodiment provides a fermentation apparatus 1 which takes care about the quality of water, and it is able to filter out impurities, condensed water or lipids which are larger than 1 μm in the air. The products of fermentation can be used directly without other processes. Also, the automatic operating conditions can be set regarding to varies requirements of fermentation such as the liquid level in the tank, heating temperature, fermentation process, mixing period, washing process, and the communication of SIM card. To sum up, this invention is not only to provide a simple and automatic fermentation apparatus, but also can be configured in large farms. It is easy and convenient to do fertilizations. The automatic washing process also conserves human resources and time on washing the fermentation tank 10, avoiding the damage caused by humans.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A fermentation apparatus comprises:
   a fermentation tank, comprising a mixer and a ventilation pore;
   a water filter, comprising a water storage barrel, a water softener and a reverse osmosis apparatus, wherein the water storage barrel is connected with the fermentation tank via at least one pipe, and wherein the reverse osmosis apparatus is connected between the water softener and the water storage barrel via the at least one pipe;
   a heater, connecting to the water filter; and
   a centrifugal pump, connecting to the water filter and the fermentation tank via the at least one pipe.

2. The fermentation apparatus as claimed in claim 1, wherein a material entrance, at least one liquid gate and a level gauge are configured on the fermentation tank.

3. The fermentation apparatus as claimed in claim 1, wherein the water filter further comprises a sand filter, an active carbon filter and a salt barrel, and wherein the sand filter is connected with the active carbon filter, the active carbon filter is connected with the water softener, and the salt barrel is connected with the water softener.

4. The fermentation apparatus as claimed in claim 1, wherein the heater is an electrothermal apparatus.

5. The fermentation apparatus as claimed in claim 1, wherein the at least one pipe comprises valves and pipe fittings.

6. The fermentation apparatus as claimed in claim 1, wherein the fermentation apparatus further comprises a control system which electrically connects to the fermentation tank, the heater, the centrifugal pump and the water filter independently.

7. The fermentation apparatus as claimed in claim 6, wherein the fermentation apparatus further comprises an air filter, connecting the ventilation pore of the fermentation tank, and wherein the air filter is electrically connected with the control system.

8. The fermentation apparatus as claimed in claim 7, wherein the air filter comprises a blower.

9. The fermentation apparatus as claimed in claim 6, wherein the fermentation apparatus further comprises a cooling apparatus, and wherein the cooling apparatus connects to the water storage barrel with the at least one pipe, the cooling apparatus electrically connects to the control system.

10. The fermentation apparatus as claimed in claim 9, wherein the cooling apparatus is an ice water machine.

11. The fermentation apparatus as claimed in claim 6, wherein the control system comprises a main circuit box and an operating circuit box, and wherein the main circuit box electrically connects to the operating circuit box.

12. The fermentation apparatus as claimed in claim 11, wherein the operating circuit box comprises a display unit and a control unit, and wherein the display unit is connected with the control unit; the display unit is a touch panel and the control unit is a multi-function chip or programmable logic controller.

13. The fermentation apparatus as claimed in claim 12, wherein the operating circuit box further comprises a communication unit, and wherein the communication unit is connected with the control unit; wherein the communication unit is a subscriber identity module (SIM) card.

14. The fermentation apparatus as claimed in claim 12, wherein the operating circuit box further comprises a communication unit; wherein the communication unit is a subscriber identity module (SIM) card.

15. The fermentation apparatus as claimed in claim 12, wherein the operating circuit box further comprises RFID (radio-frequency identification) tag recognition unit, and wherein the RFID tag recognition unit is connected with the control unit; wherein the RFID tag recognition unit is an RFID tag reader.

* * * * *